(12) United States Patent
Holmes et al.

(10) Patent No.: US 6,204,223 B1
(45) Date of Patent: Mar. 20, 2001

(54) PACKAGED AGROCHEMICAL COMPOSITION

(75) Inventors: Peter Holmes, Sheerness; Richa Shaunak, Kingshill; Rowena Roshanthi Landham, Tunstall; Rupert Heinrich Sohm, East Peckham, all of (GB)

(73) Assignee: Zeneca Limited (GB)

( * ) Notice: Subject to any disclaimer, the term of this patent is extended or adjusted under 35 U.S.C. 154(b) by 0 days.

(21) Appl. No.: 09/091,764

(22) PCT Filed: Jan. 3, 1997

(86) PCT No.: PCT/GB97/00001

§ 371 Date: Jun. 19, 1998

§ 102(e) Date: Jun. 19, 1998

(87) PCT Pub. No.: WO97/27743

PCT Pub. Date: Aug. 7, 1997

(30) Foreign Application Priority Data

Jan. 30, 1996 (GB) .................................................. 9601793
Jul. 24, 1996 (GB) .................................................. 9615540

(51) Int. Cl.⁷ ............................. A01N 25/04; B65D 85/84
(52) U.S. Cl. .................. 504/366; 206/524.4; 206/524.7; 424/455; 252/194; 504/206; 504/235; 504/250; 516/107
(58) Field of Search ........................... 516/107; 424/455; 504/116, 366, 206, 235, 250; 252/194; 206/524.4, 524.7

(56) References Cited

U.S. PATENT DOCUMENTS

| 2,990,333 | * | 6/1961 | Graham . | |
| 3,186,869 | | 6/1965 | Friedman . | |
| 3,322,674 | | 5/1967 | Freidman . | |
| 3,376,199 | * | 4/1968 | Coles et al. | 424/455 X |
| 3,892,905 | | 7/1975 | Albert | 428/220 |
| 5,037,698 | * | 8/1991 | Brunel | 252/194 X |
| 5,658,851 | * | 8/1997 | Murphy et al. | 504/116 |
| 5,928,563 | * | 7/1999 | Klima | 504/116 X |

FOREIGN PATENT DOCUMENTS

| 0 079 248 | 5/1983 | (EP) . |
| 0 199 034 | 10/1986 | (EP) . |
| 0 518 689 | 12/1992 | (EP) . |
| 954602 | 2/1962 | (GB) . |
| WO 92/01377 | 2/1992 | (WO) . |
| WO 96/03038 | 2/1996 | (WO) . |

* cited by examiner

Primary Examiner—Richard D. Lovering
(74) Attorney, Agent, or Firm—Thomas R. Savitsky

(57) ABSTRACT

An agrochemical composition packaged in a water soluble or water dispersible sachet is taught. The agrochemical composition is comprised of water-soluble, agrochemically active agent, water and an agent to minimize water loss through the walls of the sachet, wherein the is an ester of an alkyl, alkenyl, aryl, or arylalkyl acid; an ester or a naturally occurring oil; or a mineral or a synthetic oil; provided that the agent is not dibutylphtalate.

11 Claims, No Drawings

PACKAGED AGROCHEMICAL COMPOSITION

This application is a 371 of PCT/GB97/00001 filed Jan. 3, 1997.

The present invention relates to a packaged agrochemical composition comprising a water-soluble, agrochemically active ingredient, the composition being packaged in a water-soluble or water-dispersible sachet.

A gel (comprising a hazardous product, a surfactant, an acrylic acid polymer or copolymer and water) which is suitable for packaging in a water-soluble sachet is disclosed in WO92/01377. An aqueous composition, comprising a hazardous product, an electrolyte and water and packaged in a water-soluble bag, is disclosed in EP-A1-0518689. It has been found that, when the aqueous compositions of the prior art are packaged in water-soluble sachets (such as sachets made from polyvinyl alcohol), water from the composition permeates through the wall of the sachet. The water that permeates can affect the outer surface of the sachet (for example by causing the bag to dissolve or adhere to the secondary packaging) and, thereby, reduce the shelf-life of the packaged product.

Water-soluble films comprising a barrier coating are disclosed in U.S. Pat. Nos. 3,186,869, 3,322,674 and GB-954602, whilst water-soluble films comprising a layer of particulate inert plastics material having high water repellency are disclosed in EP-A2-0079248.

The present invention provides an agrochemical composition packaged in a water-soluble or water-dispersible sachet, the agrochemical composition comprising a water-soluble, agrochemically active ingredient, water and an agent to minimise water loss through the walls of the sachet.

In one aspect the present invention provides an agrochemical composition packaged in a water-soluble sachet, the agrochemical composition comprising a water-soluble, agrochemically active ingredient, water and an agent to minimise water loss through the walls of the sachet.

In a further aspect the present invention provides an agrochemical composition packaged in a water-soluble or water-dispersible sachet obtained by packing a composition comprising a water-soluble, agrochemically active ingredient, water and an agent to minimise water loss through the walls of the sachet in a water-soluble or water-dispersible sachet.

The agent to minimise water loss through the walls of the sachet is, for example, an alkyl, alkenyl, aryl or arylalkyl acid or a salt or ester thereof; an ester of a naturally occurring oil; a mineral or synthetic oil; an alcohol, an ether of an alcohol or a glyceride. It is preferred that the agent is an ester of an alkyl, alkenyl, aryl or arylalkyl acid; an ester of a naturally occurring oil; or a mineral or synthetic oil.

Aryl, and the aryl moiety of arylalkyl, is, preferably, phenyl. Aryl (especially phenyl) is optionally substituted with alkyl, alkenyl, alkynyl, phenylalkyl, phenylalkenyl or phenylalkynyl.

Alkyl groups are straight or branched chain and preferably contain from 1 to 24 carbon atoms. Alkyl is, for example, octyl, nonyl, decyl or dodecyl.

The alkyl group of arylalkyl or phenylalkyl is straight or branched chain and preferably contains from 1 to 20 (for example 1 to 10) carbon atoms.

Alkenyl groups, and the alkenyl moiety of phenylalkenyl, are straight or branched chains and preferably contain from 2 to 24, especially from 10 to 20, carbon atoms and 1, 2 or 3 double bonds. Alkenyl is, for example, stearyl, linolenyl, linolyl, licosenyl, erucyl, palmitolyl, oleyl or undecenyl.

Alkynyl groups, and the alkynyl moiety of phenylalkynyl, are straight or branched chains and preferably contain from 2 to 24, especially from 10 to 20, carbon atoms and 1, 2 or 3 triple bonds.

Suitable acid groups include carboxylic acids and sulphonic acids.

Salts include alkali metal salts such as sodium or potassium salts.

Esters include alkyl esters.

Naturally occurring oils include oils extracted from plants, seeds, nuts animals or fish and these are, for example, canola, sunflower or peanut oil. Such oils are, essentially, mixtures of esters of several unsaturated carboxylic acids. For example, sunflowerate includes esters of C18 unsaturated carboxylic acids. Other naturally occurring oils include derivatives of stearic, linolenic, linolic, licosenic, erucic, palmitic, oleic or undecenic acid.

Mineral oils include paraffin oils. Suitable mineral oils include, for example, ISOPAR® M or EXXSOL®-D110 (both available from EXXON), or SUNSPRAY® 6N or SUNSPRAY® 11N (both available from Sun Lubricants Limited, UK).

Synthetic oils include oils comprising $C_{6-24}$ alkyl, $C_{6-24}$ alkenyl or a fatty acid derivative (such as a derivative (especially an ester, such as a $C_{1-6}$ alkyl ester) of stearic, linolenic, linolic, licosenic, erucic, palmitic, oleic or undecenic acid).

Alcohols include straight or branched chain alcohols (such as glycerols) while ethers of alcohols include ethers of oleyl alcohol.

The water-soluble agrochemically active ingredient, is, for example, a herbicide (such as a paraquat salt (for example paraquat dichloride or paraquat bis (methylsulphate), a diquat salt (for example diquat dibromide or diquat alginate) or glyphosate or a salt or ester thereof (such as glyphosate isopropylammonium, glyphosate sesquisodium or glyphosate trimesium (also known as sulfosate)), an insecticide or a fungicide. It is preferred that the water-soluble agrochemical is paraquat dichloride, diquat dibromide, glyphosate isopropylammonium or glyphosate trimesium (also known as sulfosate).

An electrolyte can be added to the composition to increase its ionic strength. The electrolyte helps to improve the insolubility of the material from which the sachet is made in the composition. (See polyvinyl Alcohol—Properties and Applications pages 38–43, edited by C. A. Finch, published by J Wiley & Sons in 1973 and EP-A1-0518689.) Suitable electrolytes may, for example, comprise a cation or mixtures of cations selected from the list comprising: ammonium, copper, iron, magnesium, potassium and sodium; and an anion or mixture of anions selected from the list comprising: sulphate, nitrate, fluoride, chloride, bromide, iodide, acetate, tartrate, ammonium tartrate, benzenesulphonate, benzoate, bicarbonate, carbonate, bisulphate, bisulphite, sulphate, sulphite, borate, borotartrate, bromate, butyrate, chlorate, camphorate, chlorite, cinnamate, citrate, disilicate, dithionate, ethylsulphate, ferricyanide, ferrocynanide, fluorosilicate, formate, glycerophosphate, hydrogenphosphate, hydroxostannate, hypochlorite, hyponitrite, hypophosphite, iodate, isobutyrate, lactate, laurate, metaborate, metasilicate, methionate, methylsulphate, nitrite, oleate, orthophosphate, orthophosphite, orthosilicate, oxalate, perborate, perchlorate, phosphate, polyfluoride, polychloride, polyiodide, polybromide, polysulphide, polysulphate, polysulphite, salicylate, silicate, sorbate, stannate, stearate, succinate or valerate. Preferred electrolytes are ammonium sulphate, sodium sulphate, potassium sulphate, copper sulphate, ammonium nitrate, sodium nitrate, magnesium sulphate, potassium citrate, potassium nitrate, sodium chloride or potassium chloride.

Thus in another aspect the present invention provides an agrochemical composition packaged in a water-soluble or water-dispersible sachet, the agrochemical composition comprising a water-soluble, agrochemically active ingredient, an electrolyte, water and agent to minimise water loss through the walls of the sachet.

The agrochemical composition may be in the form of a liquid (which may be thickened using known thickeners) or a gel (gelation may be achieved by using known methods, such as methods described in WO92/01377, EP-A1-0518689 or WO96/03038).

In another aspect the present invention provides an agrochemical composition packaged in a water-soluble or water-dispersible sachet, wherein the agent to minimise water loss through the walls of the sachet is a salt (especially an alkali metal salt) or ester (especially an alkyl ester) of an alkyl, alkenyl, phenyl or phenylalkyl acid (especially a carboxylic or sulphonic acid); an alcohol or an ether of an alcohol.

In a further aspect the present invention provides an agrochemical composition packaged in a water-soluble or water-dispersible sachet, wherein the agent to minimise water loss through the walls of the sachet is a salt (especially a sodium salt) or ester (especially $C_{1-20}$ alkyl ester) of an alkyl, alkenyl or phenyl (wherein the phenyl group is optionally substituted with alkyl) acid (especially a carboxylic (such as oleic or adipic) or sulphonic (such as dodecylbenzene sulphonic) acid).

In a still further aspect the present invention provides an agrochemical composition packaged in a water-soluble or water-dispersible sachet, wherein the agent to minimise water loss through the walls of the sachet is a $C_{1-12}$ alkyl ester of an alkyl or alkenyl carboxylic acid (for example methyl oleate, ethyl oleate or di-2-ethylhexyl adipate), or a $C_{1-6}$ alkyl ester of an oil extracted from naturally occurring plants or seeds (such as methyl canolate (derived from canola oil) or methyl sunflowerate (derived from sunflower oil)).

Depending on the nature of the water-soluble, agrochemically active ingredient, one or more adjuvants or co-formulants (such as a wetter or anti-freezing agent) may also be comprised in the composition. Suitable adjuvants include neutral or anionic surfactants [such as a soap, a salt of an aliphatic monoester of sulphuric acid (for example, sodium lauryl sulphate), a salt of a sulphonated aromatic compound (for example, sodium dodecylbenzenesulphonate) or an alkyl glucoside] or polysaccharides. Suitable wetters include an alkyl glucoside (such as AL2042), a salt of a sulphonated aromatic compound (for example, sodium dodecylbenzenesulphonate), an alcohol ethoxylate or a diglucamide. Suitable thickeners include grades of xanthan gum (such as KELTROL® BT and KELZAN®).

In a further aspect the agrochemical composition also comprises a chelating or sequestering agent for calcium ions. A suitable chelating or sequestering agent is ethylenediaminetetraacetic acid (EDTA).

Over and above the components already mentioned, the agrochemical composition may also comprise an adhesive, an antifoaming agent, a buffer, a deodorant, a dye, an emetic, a preservative, an odourant, a perfume, a safener, a further solvent, a stabiliser, a synergist, a thickener or a wetting agent.

The water-soluble or water-dispersible sachet can be made from a variety of materials and preferred materials are polyethylene oxide, methyl cellulose or, especially, polyvinylalcohol (PVA). The PVA is generally partially or fully alcoholysed or hydrolysed, for example 40–100%, especially 80–100%, alcoholysed or hydrolysed polyvinyl acetate film. The PVA film may be a laminate of two or more thicknesses of film, a surface modified film (for example a film having a waxy layer) or a co-extruded film (such as is described in WO 94/29188). Preferred PVA films include M7030 (a monolayer film), L7030 (a laminate film), M7031 (a monolayer film), L7031 (a laminate film) and M9500 (also referred to as PXP2841, a monolayer film) all available from Chris Craft Industrial products Inc. of South Holland, Ill., USA.

The water-soluble or water-dispersible sachet can be formed and filled using standard techniques (such as thermoforming or vertical form-fill-sealing).

In use the packaged agrochemical composition is mixed with water (for example in an agrochemical sprayer) to give a sprayable solution of the water-soluble agrochemically active ingredient.

The packaged agrochemical composition of the present invention can be part of a bag-in-bag arrangement (for example as described in WO 92/17381 or WO 92/17383), part of an arrangement where two water-soluble sachets are joined at a common seal, part of an arrangement as described in Research Disclosure 38534 (published May 1996) or part of a bag-in-bag arrangement where the packaged agrochemical composition of the present invention is enclosed within a second water-soluble sachet holding only the packaged agrochemical composition of the present invention (the second sachet presenting a further barrier to contain the agrochemical composition).

Example 1 is an example of a composition that does not comprise an agent to minimise water loss through the walls of the sachet. Examples 2–8 illustrate the invention.

EXAMPLE 1

| Component | Function | Concentration (g/l) |
|---|---|---|
| Paraquat dichloride | Active ingredient | 200 |
| Emetic | Emetic | 0.5 |
| AL2042 (Note 1) | Surfactant | 100 |
| "Dried" Magnesium sulphate | Electrolyte | 140 |
| KELTROL ® BT (Note 2) | Gelling agent | 3 |
| SILCOLAPSE ® 5020 | Antifoam | 1 |
| SULFACIDE ® blue 5J | Colour | 5 |
| Sodium hydroxide | pH adjuster | To pH 7 |
| Water | Make-up solvent | To 1 liter |

Note 1: AL2042 is a proprietary blend of alkyl polyglucoside and ethoxylated amine surfactants supplied by ICI Surfactants.
Note 2: KELTROL ® BT is a salt tolerant grade of xanthan gum supplied by Kelco.

The composition was prepared by dissolving the paraquat dichloride and emetic in all but 25 ml of the total volume of water required. The KETROL® BT was then added while stirring. Once fully dispersed the mixture was allowed to stand without stirring for 20 minutes to allow gel strength to build up. The AL2042, magnesium sulphate, SULFACIDE® blue and SILCOLAPSE® were then added sequentially with stirring. Sodium hydroxide (40% solution) was then added to adjust pH to 7. Finally, water was added, with mixing, to bring the volume up to 1l.

EXAMPLES 2–8

| Component | Function | Concentration (g/l) |
|---|---|---|
| Paraquat dichloride | Active ingredient | 200 |
| Emetic | Emetic | 0.5 |
| AL2042 | Surfactant | 100 |
| "Dried" Magnesium sulphate | Electrolyte | 140 |
| KELTROL® BT | Gelling agent | 3 |
| See TABLE I | Permeation inhibitor | 50 |
| SILCOLAPSE® 5020 | Antifoam | 1 |
| SULFACIDE ' blue 5J | Colour | 5 |
| Sodium hydroxide | pH adjuster | To pH 7 |
| Water | Make-up solvent | To 1 liter |

The composition was prepared by dissolving the paraquat dichloride and emetic in all but 75 ml of the total volume of water required. The KELTROL® BT was then added while stirring. Once fully dispersed the mixture was allowed to stand without stirring for 20 minutes to allow gel strength to build up. The AL2042, magnesium sulphate, SULFACIDE® blue and SILCOLAPSE® were then added sequentially with stirring. Sodium hydroxide (40% solution) was then added to adjust pH to 7. The permeation inhibitor was added with mixing. Finally, water was added, with mixing, to bring the volume up to 1l.

The permeation inhibitors are as in Table I.

TABLE I

| EXAMPLE No. | PERMEATION INHIBITOR | AVAILABLE FROM |
|---|---|---|
| 2 | CRODAMOL ® CAP | Croda Chemicals |
| 3 | Ethyl oleate | Croda Chemicals |
| 4 | NANSA ® HS90S | Albright and Wilson |
| 5 | PRIOLUBE ® 1403 | Unichema International |
| 6 | Emery 2231 | Henkel |
| 7 | Emery 2230 | Henkel |
| 8 | CRODAMOL ® DOA | Croda Chemicals |

CRODAMOL ® CAP is a proprietary blend of branched chain esters
NANSA ® HS90S is sodium dodecylbenzene sulphonate (90% active)
Emery 2231 is a methylated canola oil
Emery 2230 is a methylated sunflower oil
PRIOLUBE ® 1403 is methyl oleate
CRODAMOL ® DOA is di-2-ethylhexyl adipate

EXAMPLE 9

A quantity (around 50 g) of each of the compositions from Examples 1–8 was packed into a water-soluble sachet made from M7030 grade polyvinyl alcohol film (76 micron thickness, supplied by Chris Craft). Each packed water-soluble sachet was uniquely labelled and accurately weighed on an analytical balance. Each packed, weighed sachet was placed in an individual polythene/aluminium/paper secondary pack which was sealed. Two sealed packs of each composition were placed in a constant temperature oven at 40° C. and stored for 4 weeks.

Following storage each pack was allowed to reach ambient laboratory conditions. The secondary pack was carefully opened and any signs of permeation of the water-soluble sachet noted. The external surface of the sachet was wiped, the water-soluble sachet was re-weighed, and the % weight loss calculated. The findings are presented in TABLE II.

TABLE II

| EXAMPLE No. | Replicate No. | Initial Weight (g) | Final Weight (g) | Weight Loss (%) |
|---|---|---|---|---|
| 1* | 1 | 51.6636 | 51.2150 | 0.87 |
| 1* | 2 | 52.8301 | 52.1413 | 1.30 |
| 2* | 1 | 49.3533 | 49.2215 | 0.27 |
| 2* | 2 | 48.2992 | 48.1415 | 0.32 |
| 3* | 1 | 46.6707 | 46.4283 | 0.52 |
| 3* | 2 | 45.7361 | 45.5910 | 0.32 |
| 4* | 1 | 49.2898 | 49.0820 | 0.42 |
| 4* | 2 | 51.0974 | 50.8878 | 0.41 |
| 5* | 1 | 49.5055 | 49.3089 | 0.40 |
| 5* | 2 | 50.3473 | 50.1688 | 0.35 |
| 5** | 1 | 51.8850 | 51.7806 | 0.20 |
| 5** | 2 | 52.5036 | 52.3752 | 0.24 |
| 6* | 1 | 47.5367 | 47.3411 | 0.41 |
| 6* | 2 | 52.0131 | 51.7638 | 0.48 |
| 7* | 1 | 47.9182 | 47.7441 | 0.36 |
| 7* | 2 | 56.3024 | 56.1232 | 0.32 |
| 8* | 1 | 53.9247 | 53.7520 | 0.32 |
| 8* | 2 | 49.1725 | 49.0110 | 0.33 |

*Shiny side of film (forming water-soluble sachet) is on the inner surface of the sachet.
**Shiny side of film (forming water-soluble sachet) is on the outer surface of the sachet.

EXAMPLE 10

A composition containing the following components was prepared using the method described for Examples 2–8.

| Component | Function | Concentration (g/l) |
|---|---|---|
| Paraquat dichloride | Active ingredient | 200 |
| Emetic | Emetic | 0.5 |
| AL2042 | Surfactant | 100 |
| Magnesium sulphate hydrate ($MgSO_4 \cdot 7H_2O$) | Electrolyte | 234 |
| KELTROL ® BT | Gelling agent | 3 |
| PRIOLUBE ® 1403 | Permeation inhibitor | 50 |
| SILCOLAPSE ® 5020 | Antifoam | 1 |
| SULFACIDE ® blue 5J | Colour | 5 |
| Sodium hydroxide | pH adjuster | To pH 6.5–7 |
| Water | Make-up solvent | To 1 liter |

Quantities (around 50 g) of this composition were packaged in water-soluble sachets of various films and stored according to the methodology described in Example 9. The L7030 film was 76 microns thick while the M7031 and M9500 films were both 50 microns thick. The results are shown in TABLE III.

TABLE III

| Film | Replicate no. | Initial weight (g) | Final weight (g) | Weight Loss (%) |
|---|---|---|---|---|
| L7030 | 1 | 51.2962 | 51.1689 | 0.25 |
| L7030 | 2 | 53.2853 | 53.1292 | 0.29 |
| M7031 | 1 | 49.9788 | 49.8286 | 0.30 |
| M7031 | 2 | 50.5838 | 50.4297 | 0.30 |
| M9500 | 1 | 50.1853 | 49.9749 | 0.42 |
| M9500 | 2 | 49.6982 | 49.4956 | 0.41 |

EXAMPLE 11

A composition containing the following components was prepared using the method described for Examples 2–8.

| Component | Concentration (g/l) |
|---|---|
| Diquat dibromide | 140 |
| AL2042 | 100 |
| Magnesium sulphate hydrate (MgSO$_4$.7H$_2$O) | 234 |
| KELTROL ® BT | 3 |
| SILCOLAPSE ® 5020 | 1 |
| SULFACIDE ® blue 5J | 5 |
| Methyl oleate (permeation inhibitor) | 50 |
| Sodium hydroxide (40% solution) | to pH 6.5–7.0 |
| Water | to 1 liter |

Quantities (around 50 g) of this composition were packaged in three water-soluble sachets of M7031 film (50 microns thick) and stored according to the methodology described in Example 9. At the end of four weeks it was found that the weight loss (%) for each of the three sachets was: 0.16, 0.04 and 0.08.

When methyl oleate was omitted from the composition, and that composition was packed and stored as described above, it was found that the weight loss (%) for each of the three sachets was: 2.67, 2.45 and 1.7.

EXAMPLES 12 AND 13

Table IV presents the components for two compositions containing the components listed in the amounts shown. The compositions were prepared using the method described for Examples 2–8. Quantities (around 50 g) of these compositions were packaged (in triplicate) in water-soluble sachets of M7031 film (50 microns thick) and stored according to the methodology described in Example 9. At the end of four weeks the weight loss (%) for each sachet was assessed. The bracketed weight loss data represent weight losses (%) for the situation where methyl oleate was omitted from the compositions.

TABLE IV

| Example No. | 12 | 13 |
|---|---|---|
| Component | | |
| Sulfosate (g) | 300 | |
| Glyphosate (g) | | 240 |
| Al2042 (g) | 100 | |
| Ammonium sulphate (g) | 241 | 241 |
| KELTROL ® BT (g) | 3 | 3 |
| SILCOLAPSE ® 5020 (g) | 1 | 1 |
| SULFACIDE ® blue 5J (g) | 5 | 5 |
| Methyl oleate (g) | 50 | 50 |
| Water | to 1 liter | to 1 liter |
| Weight Loss (%) | | |
| Replicate a | 0.02 (0.08) | 0.02 (0.16) |
| Replicate b | 0.00 (0.06) | 0.10 (1.23) |
| Replicate c | 0.04 (0.12) | 0.08 (0.31) |

EXAMPLES 14–20

Table V presents the components for compositions containing the components listed in the amounts shown. The compositions were prepared using the method described for Examples 2–8. Quantities (around 50 g) of these compositions were packaged (in triplicate) in water-soluble sachets of M7031 film (50 microns thick) and stored according to the methodology described in Example 9. At the end of four weeks the weight loss (%) for each sachet was assessed. Bracketed weight loss data represent weight losses (%) for the situation where the permeation inhibitor was omitted from certain compositions.

TABLE V

| | Example No. | | | | | | |
|---|---|---|---|---|---|---|---|
| | 14 | 15 | 16 | 17 | 18 | 19 | 20 |
| Component | | | | | | | |
| Paraquat dichloride (g) | 200 | 200 | 200 | 200 | 200 | 200 | 200 |
| AL2042 (g) | 100 | 100 | 100 | 100 | 100 | 100 | 100 |
| Magnesium sulphate 7H$_2$O (g) | 234 | | 234 | 234 | 234 | 234 | |
| Ammonium sulphate (g) | | 234 | | | | | |
| Tripotassium citrate (g) | | | | | | | 350 |
| KELTROL ® BT (g) | | | 3 | 3 | | 3 | |
| KELZAN ® (g) | 3 | 3 | | | | | 3 |
| SILCOLAPSE ® 5020 (g) | 1 | 1 | 1 | 1 | 1 | 1 | 1 |
| SULFACIDE ® blue 5J (g) | 5 | 5 | 5 | 5 | 5 | 5 | 5 |
| Methyl oleate (g) (permeation inhibitor) | 50 | 50 | | | | | |
| ISOPAR ® M (g) (permeation inhibitor) | | | 50 | | 50 | | 50 |
| Heated methyl oleate * (g) (permeation inhibitor) | | | | 50 | | | |
| Methyl oleate + EDTA (g) (permeation inhibitor + chelating agent) | | | | | | 50 | |
| Sodium hydroxide 40% solution | to pH 6.5–7.0 | to pH 6.5–7.0 | to pH 6.5–7.0 | to pH 6.5–7.0 | to pH 6.5–7.0 | to pH 6.5–7.0 | to pH 6.5–7.0 |
| Water | to 1 liter | to 1 liter | to 1 liter | to 1 liter | to 1 liter | to 1 liter | to 1 liter |
| Weight loss (%) | | | | | | | |
| Replicate a | 0.02 | 0.11 (0.42) | 0.02 | 0.04 | 0.09 | 0.2 | 0.1 (0.21) |
| Replicate b | 0.04 | 0.06 (0.53) | 0.06 | 0.04 | 0.08 | 0.07 | 0.02 (0.18) |
| Replicate c | 0 | 0.15 (0.49) | 0.06 | 0.06 | 0.08 | 0.08 | 0.02 (0.19) |

*Heated at 100° C. for 7 days

What is claimed is:

1. An agrochemical composition packaged in a water-soluble or water-dispersible sachet, the agrochemical composition comprising a water-soluble, agrochemically active ingredient, water and an agent to minimise water loss through the walls of the sachet wherein said agent is an ester of an alkyl, alkenyl, aryl or arylalkyl acid; an ester of a naturally occurring oil; or a mineral or synthetic oil; provided that said agent is not dibutylphthalate.

2. An agrochemical composition packaged in a water-soluble sachet as claimed in claim 1, wherein the agrochemical composition additionally includes an electrolyte.

3. An agrochemical composition packaged in a water-soluble or water-dispersible sachet as claimed in claim 1, wherein the agent to minimise water loss through the walls of the sachet is a $C_{1-12}$ alkyl ester of an alkyl or alkenyl carboxylic acid or a $C_{1-6}$ alkyl ester of an oil extracted from naturally occurring plants or seeds.

4. An agrochemical composition packaged in a water-soluble or water-dispersible sachet as claimed in claim 1, wherein the agent to minimise water loss through the walls of the sachet is methyl oleate, ethyl oleate, di-2-ethylhexyl adipate, methyl canolate or methyl sunflowerate.

5. An agrochemical composition packaged in a water-soluble or water-dispersible sachet as claimed in claim 1, wherein the sachet is made of partially or fully alcoholysed or hydrolysed polyvinyl acetate film.

6. A method of using an agent to minimize water loss through the walls of a water-soluble or water-dispersible sachet comprising the steps of:

(a) preparing an agrochemical composition comprising the agent to minimize water loss, a water-soluble, agrochemically active ingredient and water; and (b) packaging said composition in said sachet;

wherein the agent is an alkyl, alkenyl, aryl, or arylalkyl acid or a salt or ester thereof; an ester of a naturally occurring oil; a mineral or synthetic oil; an alcohol, an ether of an alcohol or a glyceride; and the sachet is made of polyethylene oxide, methyl cellulose or polyvinyl alcohol.

7. A method as claimed in claim 6 wherein the agent is an ester of an alkyl, alkenyl, aryl or arylalkyl acid; an ester of a naturally occurring oil; or a mineral or synthetic oil.

8. A method as claimed in claim 6 wherein the agent is a salt or ester of an alkyl, alkenyl or phenyl (wherein the phenyl group is optionally substituted with alkyl) acid.

9. A method as claimed in claim 6 wherein the agent is a $C_{1-12}$ alkyl ester of an alkyl or alkenyl carboxylic acid or a $C_{1-6}$ alkyl ester of an oil extracted from naturally occurring plants or seeds.

10. A method as claimed in claim 6 wherein the agent is methyl oleate, ethyl oleate, di-2-ethylhexyl adipate, methyl canolate or methyl sunflowerate.

11. A method as claimed in claim 6 wherein the water-soluble or water-dispersible sachet wherein the sachet is made of partially or fully alcoholysed or hydrolysed polyvinyl acetate film.

* * * * *